United States Patent [19]

Wong et al.

[11] Patent Number: 5,443,505
[45] Date of Patent: Aug. 22, 1995

[54] BIOCOMPATIBLE OCULAR IMPLANTS

[75] Inventors: Vernon G. Wong, Rockville, Md.; Frank Kochinke, San Jose, Calif.

[73] Assignee: Oculex Pharmaceuticals, Inc., Palo Alto, Calif.

[21] Appl. No.: 153,184

[22] Filed: Nov. 15, 1993

[51] Int. Cl.$^6$ .............................................. A61F 2/14
[52] U.S. Cl. ....................................... 623/4; 424/427; 424/428
[58] Field of Search ............ 623/4, 5; 604/294, 890.1, 604/891.1, 892.1; 424/426–429

[56] References Cited

U.S. PATENT DOCUMENTS

| | | | |
|---|---|---|---|
| 4,014,335 | 3/1977 | Arnold . | |
| 4,052,505 | 10/1977 | Higuchi et al. . | |
| 4,057,619 | 11/1977 | Higuchi et al. . | |
| 4,186,184 | 1/1980 | Zaffaroni . | |
| 4,190,642 | 2/1980 | Gale et al. . | |
| 4,281,654 | 8/1981 | Shell et al. . | |
| 4,300,557 | 11/1981 | Refojo et al. | 604/49 |
| 4,303,637 | 12/1981 | Shell et al. . | |
| 4,304,765 | 12/1981 | Shell et al. . | |
| 4,853,224 | 8/1989 | Wong . | |
| 4,997,652 | 3/1991 | Wong . | |
| 5,098,443 | 3/1992 | Parel et al. | 623/4 |
| 5,164,188 | 11/1992 | Wong | 424/428 |

OTHER PUBLICATIONS

Heller, "Controlled Drug Release from Poly(Ortho Esters)— A Surface Eroding Polymer," J. Controlled Release (1985) 2: 167–177.

Leong et al., "Polyanhydrides for Controlled release of Bioactive Agents," Biomaterials (1986) 7: 364–371.

Heller, "Bioerodible Hydrogels," in Hydrogels in Medicine of Pharmacy (H. A. Pepper Ed., CRE Press, Boca Raton, Fla.)(1987) 137–149.

Liu et al., "Intravitreal Liposome-Encapsulated Trifuluorothymidine in a Rabbit Model," Opthamology (1985) 94: 1155–1159.

Smith et al., "Intravitreal Sustained-Release Ganciclovir," Arch. Opthamology (1992) 110: 255–258.

*Primary Examiner*—Randy C. Shay
*Attorney, Agent, or Firm*—Bertram I. Rowland

[57] ABSTRACT

Implants comprising active agents are employed for introduction into a suprachoroidal space or an avascular region of an eye for therapeutic purposes. The administration of drags is controlled and maintained for long periods of time, while ensuring the substantial absence of significant levels outside the site of administration.

19 Claims, 1 Drawing Sheet

BIOCOMPATIBLE OCULAR IMPLANTS

TECHNICAL FIELD

Biocompatible implants are provided for treatment of ocular diseases.

BACKGROUND OF THE INVENTION

The eye is fundamentally one of the most important organs during life. Because of aging, diseases and other factors which can adversely affect vision, the ability to maintain the health of the eye becomes all important. A leading cause of blindness is the inability to introduce drugs or therapeutic agents into the eye and maintain these drugs or agents at a therapeutically effective concentration therein. Oral ingestion of a drug or injection of a drug at a site other than the eye provides the drug systemically. However, such systemic administration does not provide effective levels of the drug specifically to the eye and thus may necessitate administration of often unacceptably high levels of the agent in order to achieve effective intraocular concentrations. On the other hand, when a drug is injected into the eye, it quickly washes out or is depleted from within the eye into the general circulation. From the therapeutic standpoint, this may be as effective as giving no drug at all. Because of these inherent difficulties of delivering drugs into the eye, present medical treatments of ocular diseases are inadequate.

The need for a solution to these difficulties in ocular therapy is even more pressing in that a number of ocular diseases have now been identified, many of which are amenable to treatment if a proper mode of therapeutic delivery is available. It is therefore of great interest to develop modes of treatment which obviate the limitations of present modes of therapy.

RELEVANT LITERATURE

U.S. Pat. No. 4,853,224, issued Aug. 1, 1989, discloses biocompatible implants for introduction into an anterior segment or posterior segment of an eye for the treatment of an ocular condition. U.S. Pat. No. 5,164,188, issued Nov. 17, 1992, discloses a method of treating an ocular condition by introduction of a biodegradable implant comprising drugs of interest into the suprachoroidal space or pars plana of the eye.

Exemplary biocompatible, non-biodegradable addition polymeric compositions are described in U.S. Pat. Nos. 4,303,637; 4,304,765; 4,190,642; 4,186,184; 4,057,619; 4,052,505; 4,281,654; 4,959,217; 4,014,335; 4,668,506; 4,144,317.

Heller (1), Biodegradable Polymers in Controlled Drug Delivery, in: CRC Critical Reviews in Therapeutic Drug Carder Systems, Vol. 1, CRC Press, Boca Raton, Fla., 1987, pp 39-90, describes encapsulation employing biodegradable polymers for controlled drug delivery. For biodegradable hydrogels which may be employed in biodegradable polymeric compositions, see Heller (2), in: Hydrogels in Medicine and Pharmacy, N. A. Peppes ed., Vol. III, CRC Press, Boca Raton, Fla., 1987, pp 137-149. Heller, *J. of Controlled Release* (1985) 2:167-177; Leong et al., *BioMaterials* (1986) 7:364-371 describes polyanhydride microspheres. Jackanicz et al., *Contraception* (1973) 8:227; Yolles et al., in: Controlled Release of Biologically Active Agents, Tanquary et al., eds, Plenum Press, New York, N.Y., 1974, Chapter 3; Liu et al., *Opthamology* (1987) 94:1155-1159 and references cited therein report a study for the intravitreal use of liposomes for therapeutic treatment of eye disease. See also Cutfight et al., *Oral Surgery, Oral Medicine, and Oral Pathology* (1974) 37:142 and Shindler et al., *Contemporary Topics in Polymer Science* (1977) 2:251-289. Anderson et al., *Contraception* (1976) 13:375 and Miller et al., *J. Biomed. Materials Res.* (1977) 11:711, describe various properties of poly(dL-lactic acid).

Patents of interest include U.S. Pat. Nos. 3,416,530; 3,626,940; 3,828,777; 3,870,791; 3,916,899; 3,944,064; 3,962,414; 4,001,388; 4,052,505; 4,057,619; 4,164,559; 4,179,497; 4,186,184; 4,190,642; 4,281,654; 4,303,637; 4,304,765; 4,304,767; 4,439,198; 4,452,776; 4,474,751; 4,613,330; and 4,617,186.

SUMMARY OF THE INVENTION

Biocompatible implants which serve as drug delivery systems are introduced into a site extrinsic to the vitreous comprising a suprachoroidal space, an avascular region of an eye, such as the pars plana, or a surgically-induced avascular region to provide a therapeutically effective amount of an agent for treatment of an ocular condition. The implants may also be positioned over an avascular region so as to allow for transcleral diffusion of the drug to the desired site of treatment. The implants are provided as patches, plaques, films, rods, fibers and/or microspheres or microcapsules for precise delivery of a specific agent to interior regions of an eye.

DESCRIPTION OF THE SPECIFIC EMBODIMENTS

Figure 1:
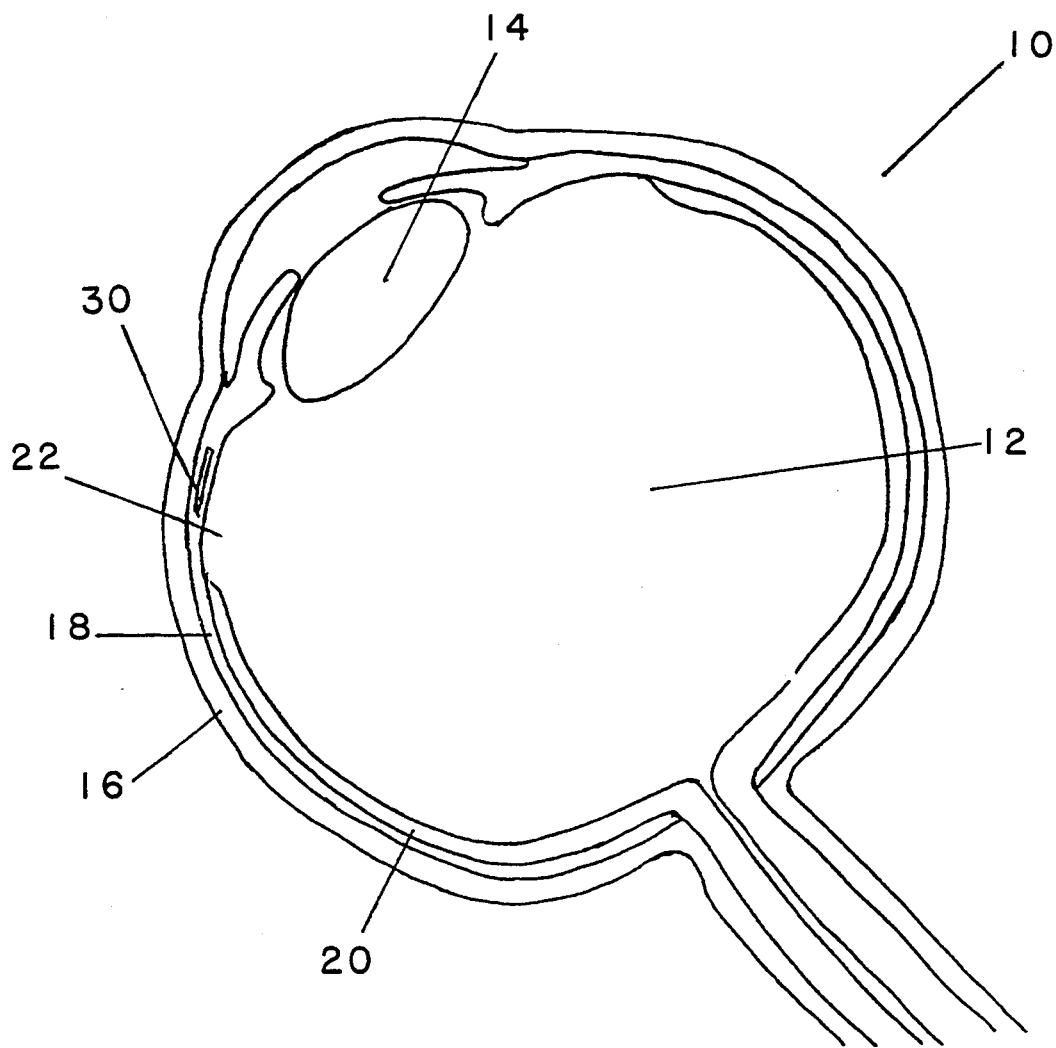
FIG. 1 is a cross-sectional view of an eye with an implant placed over the pars plana in accordance with the subject invention.

Ocular conditions, diseases, tumors and disorders, are treated by introducing slow release agent-containing biocompatible implants directly into a site substantially extrinsic to the vitreous of an eye, particularly a mammalian eye. Sites extrinsic to the vitreous comprise the suprachoroidal space, the pars plana and the like. The suprachoroid is a potential space lying between the inner scleral wall and the apposing choroid. Implants which are introduced into the suprachoroid may deliver drugs to the choroid and to the anatomically apposed retina, depending upon the diffusion of the drug from the implant, the concentration of drug comprised in the implant and the like. Of particular interest is the introduction of implants over or into an avascular region. The avascular region may be naturally occurring, such as the pars plana, or a region made to be avascular by surgical methods. Surgically-induced avascular regions may be produced in an eye by methods known in the art such as laser ablation, photocoagulation, cryotherapy, heat coagulation, cauterization and the like. It may be particularly desirable to produce such an avascular region over or near the desired site of treatment, particularly where the desired site of treatment is distant from the pars plana or placement of the implant at the pars plana is not possible. Introduction of implants over an avascular region will allow for diffusion of the drug from the implant and into the inner eye and avoids diffusion of the drug into the bloodstream;

The suprachoroid or avascular region can be entered or exposed surgically and implants placed strategically in the exposed space. Alternatively, the implants may be placed substantially on the outer surface of the eye, but positioned directly over the avascular region so as to allow for transcleral diffusion of the drug into the intraocular space. Preferably, the implants are of dimensions commensurate with the size and shape of the region selected as the site of implantation and will not migrate from the insertion site following implantation. The implants will also preferably be at least somewhat flexible so as to facilitate both insertion of the implant in the eye and accommodation of the implant by the eye. The implants may be patches, particles, sheets, patches, plaques, microcapsules and the like and may be of any size or shape compatible with the selected site of insertion. Where the implants are non-biodegradable, the implants may also comprise a refillable reservoir. The implants are formulated to include one or more agents which may be released or over an extended period of time at a therapeutically effective dosage into the interior of an eye. In this manner, agents released from the implants can reach the choroid, retina, and vitreous.

Diffusion can be further controlled so that delivery of various agents will be precise. For example where the implant is placed in the suprachoroid, delivery of a specific agent to just the underlying choroid can be controlled by the concentration of the agent in the implant and the rate of release. By increasing the concentration and diffusion rate, the agent will diffuse into the vitreous or alternatively into the apposed retina. Thus, the agent can be made available to the specific site(s) where the agent is needed and will be maintained at an effective dosage, rather than rapidly being washed out. In addition, the method of treatment of the subject invention will not require the greatly elevated levels of drug to the host to achieve an effective level in the eye, such as those required for systemic administration.

Implants comprising the agent or agents of interest to be administered to an eye are generally encapsulated or are dissolved or dispersed in a polymefic agent. Material capable of being placed in a given area without migration, such as oxycel, gelatin, silicone, etc. can also be used. The compositions will be biocompatible, and may be either biodegradable or non-biodegradable or a combination of biodegradable and nonbiodegradable polymers. The selection of the polymeric composition to be employed may vary with the site of administration, the desired period of treatment, patient tolerance, the nature of the disease to be treated and the like.

Various biocompatible, non-biodegradable polymeric compositions may be employed in the implants. The non-biodegradable polymeric composition employed must be allow for release of the drug by, for example, solution/diffusion or leaching mechanisms. The non-biodegradable polymeric compositions employed may be varied according to the compatibility of the polymer with the drug or other active agent to be employed, ease of manufacture, the desired rate of release of the drug, desired density or porosity, and the like. Various non-biodegradable polymers which may be employed are described in U.S. Pat. Nos. 4,303,637; 4,304,765; 4,190,642; 4,186,184; 4,057,619; 4,052,505; 4,281,654; 4,959,217; 4,014,335; 4,668,506; 4,144,317. The non-biodegradable polymers may be homopolymers, copolymers, straight, branched-chain, or cross-linked derivatives.

Exemplary biocompatible, non-biodegradable polymers of particular interest include polycarbamates or polyureas, particularly polyurethanes, polymers which may be cross-linked to produce non-biodegradable polymers such as cross-linked poly(vinyl acetate) and the like. Also of particular interest are ethylene-vinyl ester copolymers having an ester content of 4 to 80% such as ethylene-vinyl acetate (EVA) copolymer, ethylene-vinyl hexanoate copolymer, ethylene-vinyl propionate copolymer, ethylene-vinyl butyrate copolymer, ethylene-vinyl pentantoate copolymer, ethylene-vinyl trimethyl acetate copolymer, ethylene-vinyl diethyl acetate copolymer, ethylene-vinyl 3-methyl butanoate copolymer, ethylene-vinyl 3-3-dimethyl butanoate copolymer, and ethylene-vinyl benzoate copolymer. Ethylene-vinyl ester copolymers including ethylene-vinyl acetate copolymers for the manufacture of diffusional ocular drug delivery devices where the drug dissolves in and passes through the polymer by diffusion are described in U.S. Pat. Nos. 4,052,505 and 4,144,317.

Additional exemplary naturally occurring or synthetic non-biodegradable polymeric materials include poly(methylmethacrylate), poly(butylmethacrylate), plasticized poly(vinylchloride), plasticized poly(amides), plasticized nylon, plasticized soft nylon, plasticized poly(ethylene terephthalate), natural rubber, silicone, poly(isoprene), poly(isobutylene), poly(butadiene), poly(ethylene), poly(tetrafluoroethylene), poly(vinylidene chloride), poly(acrylonitrile, cross-linked poly(vinylpyrrolidone), poly(trifluorochloroethylene), chlorinated poly(ethylene), poly(4,4'-isopropylidene diphenylene carbonate), vinylidene chloride-acrylonitrile copolymer, vinyl chloridediethyl fumarate copolymer, silicone, silicone rubbers (especially the medical grade), poly(dimethylsiloxanes), ethylene-propylene rubber, silicone-carbonate copolymers, vinylidene chloride-vinyl chloride copolymer, vinyl chloride-acrylonitrile copolymer, vinylidene chloride-acrylonitrile copolymer, poly(olefins), poly(vinyl-olefins), poly(styrene), poly(halo-olefins), poly(vinyls), poly(acrylate), poly(methacrylate), poly(oxides), poly(esters), poly(amides), and poly(carbonates).

Biodegradable or non-biodegradable hydrogels may also be employed in the implants of the subject invention. Hydrogels are typically a copolymer material, characterized by the ability to imbibe a liquid. Exemplary non-biodegradable hydrogels which may be employed and methods of making these hydrogels are described in U.S. Pat. Nos. 4,959,217 and 4,668,506, herein incorporated by reference. Exemplary biodegradable hydrogels which may be employed are described in Heller (2), supra.

Where a non-biodegradable polymer is employed, the rate of release of the drug will be primarily solution/diffusion controlled. The rate of diffusion of drug through the non-biodegradable polymer may be affected by drug solubility, polymer hydrophilicity, extent of polymer cross-linking, expansion of the polymer upon water absorption so as to make the polymer more permeable to the drug, and the like. Diffusion of the drug from the implant may also be controlled by the structure of the implant. For example, diffusion of the drug from the implant may be controlled by means of a membrane affixed to the polymer layer comprising the drug. The membrane layer will be positioned intermediate to the polymer layer comprising the drug and the desired site of therapy. The membrane may be composed of any of the biocompatible materials indicated above and may vary with the drug employed, the presence of agents in addition to the drug present in the polymer, the composition of the polymer comprising the drug, the desired rate of diffusion and the like. For example, the polymer layer will usually comprise a very large amount of drug and will typically be saturated. Such drug-saturated polymers may generally release the drug at a very high rate. In this situation, the release of the drug may be slowed by selecting a membrane which is of a lower drug permeability than the polymer. Due to the lower drug permeability of the membrane, the drug will remain concentrated in the polymer and the overall rate of diffusion will be determined by the drug permeability of the membrane. Therefore, the rate of release of the drug from the implant is reduced, providing for a more controlled and extended delivery of the drug to the site of therapy.

Where the implant comprises a polymer layer comprising the drug and/or a membrane layer, it may be desirable for the implant to further comprise a backing layer. The backing layer will be in contact with the surfaces of the implant which are not in contact with or adjacent the desired site of therapy. For example, where the implant is a sheet, the backing layer may be present on the side of the sheet which is to be most distant from the desired site of therapy. In this instance, the backing layer may not be necessary on the edges of the sheet as the surface area of this portion of the implant is fairly insignificant and one would therefore expect loss of the drug from the polymer at this site to be minimal. The composition of the backing may vary with the drug employed in the implant, the site of implantation, compatibility with agents in addition to the drug which may be employed in the implant and the like. Of particular importance is that the backing be composed of a biocompatible, preferably non-biodegradable, material which is impermeable to the drug contained within the polymer layer. Thus diffusion of the drug from the polymer layer will only be allowed by passage through the polymer and/or membrane layer and any intervening ocular membranes to the desired site of treatment. Exemplary compositions for the backing include polyesters (e.g., mylar), polyethylene, polypropylene, teflon, aclar and other film material which are well known and/or commercially available.

The implant may further comprise an adhesive layer for securing the implant at the desired insertion site, particularly where the implant is to be placed substantially on the outer surface of the eye over an avascular region. Preferably, the adhesive layer will be on the portion of the implant in direct contact with the ocular membrane and over the desired site of treatment. Where desired, the polymer layer may be affixed to a release liner or peel strip. The release liner, which may be of any suitable material which is impermeable to the drug, will serve to prevent diffusion of the drug out of the polymer during storage. Where the implant comprises an adhesive coating, the release liner will prevent the adhesive layer from adhering to packing material, other implants, and the like. Typically the release liner will be a polyester layer coated with a release agent such as a silicone or fluorocarbon agent to facilitate removal of the release liner from the polymer prior to insertion of the implant into the eye.

For the most part, the non-biodegradable implants will have indefinite lifetimes within the eye and may be removed when either release of the drug from the polymer is complete or when therapy is no longer needed or efficacious. The period of drug administration may be varied by the amount of drug contained within the polymeric implant, the size or shape of the implant, and the like. Implant comprising non-biodegradable polymers will usually provide for diffusion of the drug for at least 2 weeks more usually at least 4 weeks, generally at least about 12 weeks and may be 24 weeks or more. The implants may be removed when therapy is completed or no longer efficacious.

Where, for example, the molecular weight of the drug, the desired dosage, the period of administration (as in chronic therapy) and the like are such that the size of the implants required to contain the desired amount of drug or drug solution is incompatible with the size of the insertion site or would compromise the patient's vision, employment of a non-biodegradable implant comprising a refillable reservoir may be desired. Non-biodegradable, refillable reservoirs may comprise a non-biodegradable outer surface and a hollow or substantially hollow center which acts as the depot, or reservoir, for the active agent. The active agent may be present in a variety of forms including initially dry; in a suspension comprising a physiological buffer such as saline, a permeability enhancing agent such as ethanol, or a preservative such as EDTA; in a suspension comprising a biodegradable polymeric composition; in a suspension comprising a biodegradable gel, or the like. The implant be refilled with any one or all of the components present in the original active agent suspension contained within the implant. The implant may be placed into the desired site of insertion, so that it will not substantially migrate from the site of insertion.

The implant may be refilled by, for example, injection of the active agent directly into the reservoir of the implant. It is of particular importance to the operability of implants comprising refillable reservoirs that refilling of the implant does not compromise the ability of the implant to release the active agent at the desired rate. Therefore, it is preferable that the outer surface of the implant will comprise a self-sealing layer. The self-sealing layer may be comprised of a non-biodegradable material and may be a rubber-like material or other material which is capable of resealing. Injection of the active agent or active agent suspension through the self-sealing layer will not result in the production of a hole at the site of injection. Alternatively, the refillable implant may comprise an inlet. The inlet may comprise a hollow fiber which may be positioned so as to communicate with the outer surface of the implant and with the reservoir within the body of the implant. The portion of the inlet which communicates with the outer surface of the implant will be of a self-sealing composition or will be capable of being reseated or otherwise treated so as to prevent loss of the drug from the reservoir through the inlet. Implants with such inlets may be refilled by injection of the active agent through the hollow fiber. In addition, where the implant is placed within the tissue layers of the eye (e.g., between the scleral layers), the inlet of the implant may be positioned so as to be accessible from the outer surface of the eye for refilling of the implant reservoir.

Following insertion, the refillable, non-biodegradable implant will provide for diffusion of the drug contained therein for at least 2 weeks, more usually at least 4 weeks, generally at least about 8 weeks and may be 6 months or more. After diffusion of the drug is complete, the reservoir may be refilled by means of injection of the drug or drug suspension into the implant. Alternatively, the implant may comprise an inlet which communicates with the outer surface of the implant and with the internal reservoir. The drug or drug suspension may then be injected through the inlet to refill the implant. An example of an implant comprising a refillable reservoir is described in U.S. Pat. No. 4,300,557. The refillable implants may be employed in the eye of the patient for the entire course of therapy and may be employed for at least 2 weeks, more usually at least 4 weeks, generally at least about 8 weeks and may be 6 months or more. The implants may be removed when therapy is completed or no longer efficacious.

Biodegradable polymeric compositions which may be employed may be organic esters or ethers, which when degraded result in physiologically acceptable degradation products, including the monomers. Anhydrides, amides, orthoesters or the like, by themselves or in combination with other monomers, may find use. The polymers may be addition or condensation polymers, particularly condensation polymers. The polymers may be cross-linked or non-cross-linked, usually not more than lightly cross-linked, generally less than 5%, usually less than 1%. For the most part, besides carbon and hydrogen, the polymers will include oxygen and nitrogen, particularly oxygen. The oxygen may be present as oxy, e.g., hydroxy or ether, carbonyl, e.g., non-oxo-carbonyl, such as carboxylic acid ester, and the like. The nitrogen may be present as amide, cyano and amino. The polymers set forth in Heller (1), supra, may find use, and that disclosure is specifically incorporated herein by reference.

Of particular interest are polymers of hydroxyaliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof. By employing the L-lactate, a slowly eroding polymer is achieved, while erosion is substantially enhanced with the lactate racemate.

Among the polysaccharides will be calcium alginate, and functionalized celluloses, particularly carboxymethylcellulose esters characterized by being water insoluble, a molecular weight of about 5 kD to 500 kD, etc. Other polymers of interest include polyvinyl alcohol, esters and ethers, which are biocompatible and may be biodegradable or soluble. For the most part, characteristics of the polymers will include biocompatibility, compatibility with the agent of interest, ease of encapsulation, a half-life in the physiological environment of at least 6 hrs; preferably greater than one day, no significant enhancement of the viscosity of the vitreous, water insoluble, and the like.

The biodegradable polymers which form the implants will desirably be subject to enzymatic or hydrolytic instability. Water soluble polymers may be cross-linked with hydrolyric or biodegradable unstable cross-links to provide useful water insoluble polymers. The degree of stability can be varied widely, depending upon the choice of monomer, whether a homopolymer or copolymer is employed, employing mixtures of polymers, where the polymers may be employed as varying layers or mixed.

By employing a biodegradable polymer, particularly one where the biodegradation is relatively slow, the rate of release of the drug will be primarily diffusion controlled, depending upon the nature of the surrounding membrane or monolithic polymer structure, rather than polymer degradation leading to disintegration of the implant. For the most part, the selected particles will have lifetimes at least equal to the desired period of administration, preferably at least twice the desired period of administration, and may have lifetimes of 5 to 10 times the desired period of administration. The period of administration will usually be at least 3 days, more usually at least 7 days, generally at least about 15 days and may be 20 days or more.

The particles for implantation may be substantially homogeneous as to composition and physical characteristics or heterogeneous. Thus, particles can be prepared where the center may be of one material and the surface have one or more layers of the same or different composition, where the layers may be cross-linked, of different molecular weight, different density or porosity, or the like. For example, the center could be a polylactate coated with a polylactate-polyglycolate copolymer, so as to enhance the rate of initial degradation. Most ratios of lactate to glycolate employed will be in the range of about 1:0.1. Alternatively, the center could be polyvinyl alcohol coated with polylactate, so that on degradation of the polylactate the center would dissolve and be rapidly washed out of the eye. Implants may also be composed of biodegradable and non-biodegradable polymers. For example, the implant may comprise an outer surface made of a non-biodegradable polymeric material surrounding an inner core of biodegradable material. the rate of release of the active agent would then be influenced by both the release of the agent from the biodegradable center and subsequent diffusion of the drug through the outer non-biodegradable layer.

Any pharmacologically active agent for which sustained release is desirable may be employed including drugs, pharmaceutical agents, bacterial agents, etc. The agents will be capable of diffusion into the vitreous to be present at an effective dose. In this manner, drugs or pharmaceutical agents will be sufficiently soluble to be presented at pharmacologically effective doses. Pharmacologic agents which may find use may be found in U.S. Pat. Nos. 4,474,451, columns 4–6, and U.S. Pat. No. 4,327,725, columns 7–8, which disclosures are incorporated herein by reference.

Bacterial agents include acid fast bacilli, (BCG), *Corynebacterium parvum*, LPS, endotoxin etc. These agents induce an immune response enhancing immune attack of tumor cells. These agents are frequently used as immune adjuvants to enhance an immune response to an administered antigen. See Morton et al., *Surgery* (1970) 68:158–164; Nathanson, L., *Cancer Chemother. Rep.* (1973) 56:659–666; Pinsky et. al., *Proc. AACR* (1972) 13:21; and, Zhar et. al., *J. Nat'l Cancer Inst.* (1971) 46:831–839.

Drugs of particular interest include hydrocortisone, gentamicin, 5-fluorouracil, sorbinil, IL-2, TNF, Phakan-a (a component of glutathione), thiolathiopronin, Bendazac, acetylsalicylic acid, trifluorothymidine, interferon ($\alpha$, $\beta$ and $\gamma$), immune modulators, e.g., lymphokines, monokines, and growth factors, cytokines, anti-(growth factors), etc.

Other drugs of interest include drugs for treatment of macular degeneration, such as interferon, particularly $\alpha$-interferon; transforming growth factor (TGF), particularlly TGF-$\beta$; insluin-like growth factos; anti-glaucoma drugs, such as the beta-blockers: timolol maleate, betaxolol and metipranolol; mitotics: pilocarpine, acetylcholine chloride, isoflurophate, demecarium bromide, echothiophate iodide, phospholine iodide, carbachol, and physostigmine; epinephrine and salts, such as dipivefrin hydrochloride; and dichlorphenamide, acetazolamide and methazolamide; anti-cataract and anti-diabetic retinopathy drugs, such as aldose reductase inhibitors: tolrestat, lisinopril, enalapril, and statil; thiol cross-linking drugs other than those considered previously; anti-cancer drugs, such as retinoic acid, methotrexate, adriarnycin, bleomycin, triamcinolone, mitomycin, cis-platinum, vincristine, vinblastine, actinomycin-D, ara-c, bisantrene, CCNU, activated cytoxan, DTIC, HMM, melphalan, mithramycin, procarbazine, VM26, VP16, and tamoxifen; immune modulators, other than those indicated previously; anti-clotting agents, such as tissue plasminogen activator, urokinase, and streptokinase; anti-tissue damage agents, such as superoxide dismutase; proteins and nucleic acids, such as monoand polyclonal antibodies, enzymes, protein hormones and genes, gene fragments and plasmids; steroids, particularly anti-inflammatory or anti-fibrous drugs, such as cortisone, hydrocortisone, prednisolone, prednisone, dexamethasone, progesterone-like compounds, medrysone (HMS) and fluorometholone; non-steroidal anti-inflammatory drugs, such as ketrolac tromethamine, diclofenac sodium and suprofen; antibiotics, such as loftdine (cephaloridine), chloramphenicol, clindamycin, amikacin, tobramycin, methicillin, lincomycin, oxycillin, penicillin, amphotericin B, polymyxin B, cephalosporin family, ampicillin, bacitracin, carbenicillin, cephalothin, colistin, erythromycin, streptomycin, neomycin, sulfacetamide, vancomycin, silver nitrate, sulfisoxazole diolamine, quinolones, and tetracycline; other anti-pathogens, including anti-fungal or anti-viral agents, such as idoxuridine, trifluorouddine, vidarabine (adenine arabinoside), acyclovir (acycloguanosine), gancyclovir, pyrimethamine, trisulfapyrimidine-2, clindamycin, nystatin, flucytosine, natamycin, miconazole, ketoconazole, aromatic diamidines (e.g., dihydroxystilbamidine) and piperazine derivatives, e.g. diethylcarbamazine; cycloplegic and mydriatic agents, such as atropine, cyclogel, scopolamine, homatropine and mydriacyl.

Other agents include anticholinergics, anticoagulants, antifibrinolytic agents, antihistamines, antimalarials, antitoxins, chelating agents, hormones, immunosuppressives, thrombolytic agents, vitamins, salts, desensitizing agents, prostaglandins, amino acids, metabolites and antiallergenics.

The amount of agent employed in the implant will vary widely depending on the effective dosage required and rate of release. Usually the agent will be from about 1 to 80, more usually 20 to 40 weight percent of the implant.

Other agents may be employed in the formulation for a variety of purposes. For example, agents which increase drug solubility, buffering agents and preservatives may be employed. Where the implant is positioned such that no portion of the implant is in direct contact with the vitreous, diffusion of the drug into the eye (for example across the conjunctiva, sclera and choroid to reach the vitreous) may be facilitated by enhancers (i.e. DMSO, detergents, ethanol, isopropyl myristate (IPM), oleic acid, azome and the like). Enhancers may act either to increase the permeability of ocular membranes through which the active agent must diffuse in order to reach the desired site within the eye or may serve to increase drug solubility within the vitreous. The enhancer employed will vary with the drug, as well as the polymer, employed in the implant. Water soluble preservatives which may be employed include sodium bisulfite, sodium thiosulfate, ascotbate, benzalkonium chloride, chlorobutanol, thimerosal, phenylmercuric borate, parabens, benzyl alcohol and phenylethanol. These agents may be present in individual amounts of from about 0.001 to about 5% by weight and preferably about 0.01 to about 2%. Suitable water soluble buffering agents which may be employed are alkali or alkaline earth carbonates, phosphates, bicarbonates, citrates, borates, acetates, succinates and the like, such as sodium phosphate, citrate, borate, acetate, bicarbonate and carbonate. These agents may be present in amounts sufficient to maintain a pH of the system of between 2 to 9 and preferably 4 to 8. As such the buffering agent may be as much as 5% on a weight to weight basis of the total composition.

The implants may also be of any geometry including fibers, sheets, films, microspheres, circular discs, plaques and the like. The upper limit for the implant size will be determined by factors such as eye toleration for the implant, size limitations on insertion into the avascular region, ease of handling, etc. Where sheets or films are employed, the sheets or films will be in the range of at least about 0.5 mm×0.5 mm, usually about 3–10 mm×5–10 mm with a thickness of about 0.25–1.0 mm for ease of handling. Where fibers are employed, the diameter of the fiber will generally be in the range of 0.1 to 1 mm. The length of the fiber will generally be in the range of 0.5–5 mm. The size and form of the implant can be used to control the rate of released period of treatment, and drug concentration in the eye. In some situations mixtures of implants may be utilized employing the same or different pharmacological agents. In this way, in a single administration a course of drug treatment may be achieved, where the pattern of release may be greatly varied.

Various techniques may be employed to produce the implants. Useful techniques include solvent evaporation methods, phase separation methods, interfacial methods, extrusion methods, molding methods, injection molding methods, heat press methods and the like.

In preparing the polymeric, drug-comprising implants, for the most part solvent-evaporation methods will be employed. Where the implants are to be in the form of microcapsules or microparticles, the preformed rate controlling polymer is dissolved in a volatile substantially water-immiscible solvent, such as chloroform, methylene chloride, or benzene. Sometimes, the water immiscible solvent will be modified with a small amount of a water-miscible organic cosolvent, particularly an oxygenated solvent, such as acetone, methanol, ethanol, etc. Usually, the water-miscible organic cosolvent will be less than about 40 vol % usually less than about 25 vol %. The agent may then be added to the polymer-solvent solution. Depending upon the nature of the agent, one may have the agent dispersed in the viscous polymer-solvent mixture or a solid dispersion of drug particles, where the drug will have been pulverized to obtain a fine powder, usually a microfine powder particularly of a size of less than about 1 mM, usually less than about 0.5 mM, and may be about 0.5 $\mu$M or smaller. Where polymefic hydrogels are employed, particularly non-biodegradable polymeric hydrogels, it may be desirable to add a catalyst to achieve polymerization of the drug-solvent solution. Methods for the production of non-biodegradable hydrogels are well known in the art and are described in U.S. Pat. Nos. 4,668,506 and 4,959,217.

The amount of polymer employed in the medium will vary with the size of the implant desired, whether additional coatings will be added, the viscosity of the solution, the solubility of the polymer and the like. Usually, the concentration of polymer will be in the range of 10 to 80 weight percent. The ratio of agent to polymer will vary with the desired rate of release, the amount of agent generally varying in the range of 1 to 80 weight percent of the polymer in addition to other agents present.

The ratio of drug to polymer may be adjusted to produce optimized compositions, since the final product will normally result in the initial ratio. By manipulating the initial bulk viscosity of the drug-polymer-solvent mixture and of the aqueous dispersing medium, the dissolved polymer agent/mixture may also be added to a rapidly stirred aqueous solution. In this instance the polymer mixture will coalesce in the absence of a dispersing agent, resulting in a large sheet or mass of encapsulation or macroencapsulation. Macroencapsulation can also be achieved when stirring of the aqueous solution during coacervation is slowed or stopped. Macrocapsules are then shaped into plaques for insertion into an eye.

In an alternative method of making the implants, a membrane coating may be formed around the layered solution to provide an encapsulated implant for controlled, prolonged release of the active agent. To form the coating, an appropriate aqueous solution, generally water, is slowly poured over the surface. In this manner, polymerization results in a membrane surrounding the drug or agent. The resulting membrane bound plaques can be cut to any size or geometry for insertion into an eye. To produce sheets of a particular dimension, the solution can be layered into preformed molds and the surface polymerized. In this manner, the implants are ready for use without having to be cut to desired sizes. Alternatively, the drug and polymer mixture may be extruded to provide, for example, a long rod or fiber. The fiber may then be cut to pieces of desired length for insertion.

The dispersion or solution can alternatively be added to a rapidly stirred aqueous solution comprising water and a dispersion agent, which may be a protective colloid. To form macromolecules, dispersing agents such as poly(vinyl alcohol) (1 to 5%) or non-ionic detergents, such as Span detergents are employed.

Implants may also be formed by mixing the agent with molten polymer at the appropriate temperature, for example for molten polylactic polymer, between 60° to 90° C. The resulting mixture can be cut, molded, injection molded or extruded into any shape or size for insertion into an eye.

The implants may also be formed by pouring or layering the active agent dispersion or solution onto a surface such as a petri plate. By variation of surface area in relationship to the volume of polymer solution, the layer can be made to conform to any desired dimensions including surface area and width. For ease in handling of the implant, the polymer solution may be directly layered onto a release liner. Where desired, the release liner may comprise an adhesive layer on the side of the liner in contact with the polymer solution. After evaporation of the solvent, a second release liner may be employed to protect the exposed portion of the implant. Where a backing layer is to be employed, the polymer solution may be layered directly onto the backing layer material and the solvent evaporated or a release liner attached to the underlying structure. Where a membrane layer is desired, a solution of the membrane polymer may be layered over the polymer layer. Where desired, a release liner may then be placed on top of the polymer layer and/or the membrane layer. Where the implant is to comprise an adhesive layer, the adhesive layer may be applied to the release liner prior to placing the release liner on the polymer layer and/or membrane layer. When the release liner is later removed prior to insertion of the implant, the adhesive layer will substantially remain on the polymer layer and/or membrane layer.

Where desired, the implant may be formed by one of the method described above, but in the absence of the active agent. The drug-free implant may then be loaded with drug by, for example, immersing the implant in a solution comprising the active agent for a time sufficient for absorption of the drug. Alternatively, where the implant comprises a hollow fiber, for example, the active agent may be directly loaded into the fiber and the implant subsequently sealed. Where the activity of the drug will not be compromised, the drug-filled implant may then be dried or partially dried for storage until use. This method may find particular application where the activity of the drug of choice is sensitive to exposure to solvents, heat or other aspects of the conventional solvent-evaporation, molding, extrusion or other methods described above.

Where a implant comprising a refillable reservoir is desired, implant may be molded in two separate portions. At least one of these separate portions may be substantially concave. The two portions, which comprise the body of the implant, may then be sealed together with a biocompatible adhesive, such as a silicone adhesive, to form an implant having a substantially hollow center which may serve as a reservoir or depot for the active agent or drug. Alternatively, implants comprising a reservoir may be produced by conventional form-fill-seal techniques. Where an inlet is desired, the inlet may be positioned in the implant prior to sealing. The refillable implant may also be manufactured employing injection molding techniques. By employing injection molding, the shape and size of the implant, the desired volume of active agent to be held within the reservoir, the presence of an inlet for refilling the implant and the like may be varied by varying the mold which receives the polymer mixture. The refillable implant may be filled with the active agent or active agent suspension after the non-biodegradable outer layer is formed. Alternatively, the implants may be co-molded so that the outer nonbiodegradable surface and the biodegradable-active agent center are formed substantially simultaneously by, for example, co-injection into a mold during injection molding.

In order to define the potential drug-release behavior of the implants in vivo, a weighed sample of the implants may be added to a measured volume of a solution containing four parts by weight of ethanol and six parts by weight of deionized water. The mixture is maintained at 37° C. and stirred slowly to maintain the implants in suspension. The appearance of the dissolved drug as a function of time may be followed spectrophotometrically until the absorbance becomes constant or until greater than 90% of the drug has been released. The drug concentration after 1 h in the medium is indicative of the amount of free unencapsulated drug in the dose, while the time required for 90% drug to be released is related to the expected duration of action of the dose in vivo. As a general rule, one day of drug release is approximately equal to 35 days of release in vivo. While release may not be uniform, normally the release will be free of larger fluctuations from some average value which allows for a relatively uniform release, usually following a brief initial phase of rapid release of the drug.

The implants may be administered into the eye in a variety of ways, including surgical means, injection, trocar, etc.

The implants may be placed substantially within the tear fluid upon the outer surface of the eye over an avascular region, and may be anchored in the conjunctiva or sclera; episclerally or intrasclerally over an avascular region; substantially within the suprachoroidal space over an avascular region such as the pars plana or a surgically-induced avascular region; or in direct communication with the vitreal chamber or vitreous so as to avoid diffusion of the drug into the bloodstream. Diffusion of the drag to the desired site may be facilitated by forming holes or tunnels through the layers of the sclera or other tissue which communicate, or substantially communicate, with the desired site of therapy which lie beneath the implant. As a result, the tunnels will lie beneath the implant and serve to substantially direct the flow of the drug from the implant to the desired site of therapy. These holes may be formed by surgical procedures which are known in the art or through the application of a permeability enhancing agent described above such as ethanol, oleic acid, isopropyl myristate and the like.

Surgical procedures, such as those known in the art, may be necessary to position large macrocapsules or plaques. For example, the implants can be inserted through a sclerotomy into the suprachoroid. In this instance, the sclera is cut to expose the suprachoroid. An implant is then inserted on either side of the incision. Alternatively, a partial-thickness scleral trap-door can be fashioned over the suprachoroid or an avascular region. An implant is then inserted and the scleral flap is sewn back into place to secure the implant.

Alternatively, the implant may be inserted so as to directly communicate with the vitreal chamber. To achieve this, a partial thickness scleral trap door flap is cut over an avascular region, such a the pars plana, to remove the eye coat. A hole (or holes) is made through the floor of the scleral bed to communicate with the base of the vitreous body through the pars plana. The implant is positioned over the hole within the scleral bed and the flap of the trap door is sewn back into place. Such placement of the implant will allow for the ready diffusion of the drug into the vitreous and into the intraocular structure.

Turning now to FIG. 1, a cross-sectional view of an eye treated with an implant in accordance with the subject invention is shown. In the center of the eye is the vitreous 12. Next to the vitreous 12 is lens 14. Adjacent to, and encompassing much of, the vitreous 12 is the optic part of the retina 20, which in turn is bordered by the choroid 18. Between the optic part of the retina 20 and the lens 14, adjacent the vitreous 12 is the pars plana 22. The choroid 18, in turn, is bordered by the sclera 16. An implant 30 is placed in the space between the choroid 18 and sclera 16 in the avascular region over the pars plana 22.

The following examples are offered by way of illustration and not by way of limitation.

EXPERIMENTAL

Choroidal Implantation

Brown-Pierce (BP) carcinoma was implanted into the choroidal bed in one eye of each of six rabbits. The tumor grew into appropriate size, simulating that of the human, within 3 to 6 weeks. Tubercle bacilli (BCG—Bacille Calmette-Guefin) $1.0 \times 10^8$ was thoroughly mixed in 2 ml of molten, biodegradable polylactic polymer between 60° to 90° C. The melted mixture was then plated and cooled at room temperature to a thickness of 0.5 to 0.75 mm. A 4 to 5 mm disc (or plaque) was trephined from the hardened polyiactate-BCG mixture. This disc or plaque was then surgically implanted into the base of the tumor. After 7 to 10 days, the size of the tumor did not increase and the tumor became discolored. Over the ensuing 6 to 8 weeks tumor resorption continued and total resolution was complete by 3 months.

Tumor reimplantation in each of the six animals in the anterior chamber, in the choroidal bed of the control eye, and infusion of $1 \times 10^7$ tumor cells intravenously was followed by no tumor growth and there was no animal morbidity. At necropsy, tumor infiltration was not observed in all major organs, including the once tumor bearing eye.

In each of six control animals, the impregnated polylactic plaques induced a corresponding local chorioretinitis with no further disturbance of the eye. On implantation of The Brown-Pierce tumor into the anterior chamber (AC) and choroidal bed, tumor growth was observed. Each of the animals succumbed to generalized metastases on subsequent infusion of $1 \times 10^7$ malignant cells.

Acid-fast bacilli (tbc) incorporated into polylactic acid eradicated intraocular BP tumor and established a specific immunity both locally and systemically against the implanted intraocular tumor.

Polylactic acid incorporated *Corynebacterium parvum* (*C. parvum*) gave identical results as those observed with polylactic acid incorporated acid-fast bacilli. 100 mg of *C. parvum* was mixed with 1000 mg of polylactate solubilized in 2 ml chloroform and 0.25 ml of ethanol. The mixture was plated over a thin layer of water to approximately 0.5 mm in thickness before a disc or plaque of 5 mm was trephined from the center of the plated mixture. Coacervation was completed by covering the plated mixture with additional water for 8 hours under low vacuum. Water was discarded and the preparation was dried in vacuum and desiccation for an additional 24 hrs. The trephined disc of coacervated *C. parvum* was surgically implanted into the base of the tumor. In each instance, tbc and *C. parrum* with polylactic acid demonstrated specific anti-tumor activity, adjuvant and immunizing properties.

Vincristine and VX2 Adenocarcinoma

Both eyes of six rabbits were implanted in the choroidal bed with VX2 adenocarcinoma. Intraocular growth simulated those of the human eye. Without treatment the tumor will grow uncontrolled with distant metastasis and ocular rupture.

Vincristine, a vinca alkaloid, known to be effective against VX2 adenocarcinoma with an in vitro $IC_{50}$ in the range of 0.002–0.003 µg/ml, was incorporated with polylactic acid. When VX2 was implanted and grew to an appropriate intraocular size of 6.5 mm × 6.5 mm (range 5.5 to 7.5 mm), polylactate incorporated vincristine was imbedded at the base of the choroidal tumor. 10 mg of Vincristine was mixed with approximately 500 mg of molten polylactate polymer and poured into a thin layer of 0.4 to 0.5 mm thickness and cooled in room temperature overnight. A disc of 5 mm was trephined from the hardened mixture and placed into the base of the choroidal tumor. The control eye received only the lactic acid polymer. Tumor regression was noted clinically within 6 to 9 days and complete resolution by 7 to 9 weeks. Tumor in the untreated control eye grew and caused tumor extension with subsequent rupture of the globe.

Pars Plana Drug Delivery

The exposure to the vitreous base at the pars plana could be performed by fashioning a full thickness scleral flap or by trephining through the bed of the sclera within a lamellar trap door. Encapsulated microspheres can be placed through the trephined hole(s) and thus into the vitreous base. Alternatively, polylactate incorporated drag formed into plaques of 3 to 5×7 to 9 mm with a thickness of 0.25 to 1.0 mm are placed within the trap door and held in place with closure of the scleral flap.

Drug Diffusion by Way of Pars Plana

One eye of each of six rabbits was implanted at the pars plana with methotrexate (MTX)-lactic acid microspheres and in one eye of another six rabbits with hydrocortisone acetate-lactic acid microspheres.

A 40% (by weight) mixture of MTX and hydrocortisone with polylactate polymer were solubilized in chloroform and ethanol (Table 1). Coacervation into microcapsules took place in 500 ml of a 5% polyvinyl alcohol aqueous solution with moderate to high speed stirring. Evaporation was performed under light vacuum with constant stirring for an additional 8 hrs. The resulting microspheres measuring 0.1 to 0.5 mm were selected and dried in vacuum for an additional 24 to 48 hours. Approximately 25 microcapsules were implanted at the pars plana.

A 40% (by weight) of MTX and hydrocortisone and polylactate polymer were mixed under moltened conditions (Table 2). The resulting mixture was plated into a thin layer of approximately 0.4 to 0.5 mm in thickness and cooled overnight at room temperature. A plaque measuring approximately 3×4 mm was fashioned from the layer and was surgically placed into the pars plana.

Results of the experiments were as follows:

TABLE 1

| # | Drug μg/ml | Assay | Time wks | RE AC | RE PC | LE AC | LE PC |
|---|---|---|---|---|---|---|---|
| 1* | MTX | EMIT | 1 | — | 0.8 | — | 0 |
| 2* | MTX | EMIT | 2 | — | 1.2 | — | 0 |
| 3* | MTX | EMIT | 3 | — | 1.4 | — | 0 |
| 4* | MTX | EMIT | 4 | — | 0.7 | — | 0 |
| 5* | MTX | EMIT | 5 | — | 1.0 | — | 0 |
| 6* | MTX | EMIT | 6 | — | 0.9 | — | 0 |
| 7* | Hydrocortisone | HPLC | 1 | — | 0 | — | 1.3 |
| 8* | Hydrocortisone | HPLC | 2 | — | 0 | — | 2.0 |
| 9* | Hydrocortisone | HPLC | 3 | — | 0 | — | 2.4 |
| 10* | Hydrocortisone | HPLC | 4 | — | 0 | — | 1.1 |
| 11* | Hydrocortisone | HPLC | 5 | — | 0 | — | 0.9 |
| 12* | Hydrocortisone | HPLC | 6 | — | 0 | — | 2.0 |

\# = Animal = Rabbit
\* = Microcapsule in pars plana
+ = Plaque in pars plana
RE = Right Eye
LE = Left Eye
AC = Anterior Chamber
PC = Posterior Chamber Plaques of MTX and hydrocortisone were given to one eye of each of 3 animals at the pars plana and over the vitreous base following scleral resection. The results are given in Table 2.

TABLE 2

| # | Drug μg/ml | Assay | Time wks | RE AC | RE PC | LE AC | LE PC |
|---|---|---|---|---|---|---|---|
| 1+ | MTX | EMIT | 1 | — | 1.5 | — | 0 |
| 2+ | MTX | EMIT | 2 | — | 4.0 | — | 0 |
| 3+ | MTX | EMIT | 3 | — | 2.0 | — | 0 |
| 4+ | Hydrocortisone | HPLC | 1 | — | 0 | — | 1.3 |
| 5+ | Hydrocortisone | HPLC | 2 | — | 0 | — | 1.9 |
| 6+ | Hydrocortisone | HPLC | 3 | — | 0 | — | 2.3 |

\# = Animal = Rabbit
\* = Microcapsule in pars plana
+ = Plaque in pars plana
RE = Right Eye
LE = Left Eye
AC = Anterior Chamber
PC = Posterior Chamber Methylcellulose Implant Comprising Dexamethasone 2 g of methylcellulose was dissolved in 5 g phosphate-buffered saline (PBS) at room temperature. Following dissolution of the polymer, 2 g dexamethasone were added and the solution mixed thoroughly. The polymer-drug mixture was then coated onto a 3M 1022 release liner and a 1 mm coating bar used to draw down a film. The film was then dried overnight under vacuum. Implants were then cut from the sheets of drug-filled polymer affixed to release liner to the desired shape and size. After removal of the release liner, a 2.2 mg implant was implanted suprachoroidally into a rabbit eye. The concentration of drug released into the vitreous was monitored for one week by HPLC analysis of vitreous samples at 24, 96, 120 and 168 hrs. After 24 hrs, dexamethasone was present in the vitreous at approximately 1.50 ppm. After 168 hrs, the concentration of the drug in the vitreous was maintained at levels approximating 1.0 ppm.

Preparation of Non-Biodegradable Implants

EXAMPLE 1

Two grams of polyurethane (Pellethane 2363-80AE) were dissolved in 8 g of 1,2,3,4-tetrahydro-9-fluorenone (THF) at room temperature with mixing. Following dissolution of the polyurethane, 2 g of dexamethasone were added and mixed thoroughly. The drug-polymer mixture was then coated onto a 3M 1022 release finer material. The resulting polymeric films were in thicknesses ranging from 250 μm to 1000 μm. After drying of the mixtures, implants were then cut from the resulting sheets of drag-filled polymer affixed to the release liner. The drag-release behavior of the polymeric, drug-containing sheets was then tested. The release liner was removed from an implant sheet and a weighed sample of the sheet added to a solution containing four parts by weight ethanol and six parts by weight of deionized water at 37° C. with slow stirring. The appearance of the dissolved drug was followed as a function of time by spectrophotometry. As expected for a polymer containing a high load of drug, more than 50% of the drug contained within the sheets was released within 4 hrs. Thus when this type of implant is placed in the eye, the rate-limiting step in drug release from the implant would be determined by the solubility of the drug in the membrane to which the implant is in contact.

EXAMPLE 2

As described above, 0.5 g polyurethane (Pellethane 2363-80AE) was dissolved in 2 g THF. Subsequently, 0.5 g gancyclovir was added and the solution mixed thoroughly. The drug-polymer solution was then layered onto a 3M 1022 release liner. After drying, implants were cut from the resulting sheets of drug-filled polymer affixed to release liner. The release liner was removed and the drug-release behavior of the drug was then tested in vitro as described above. After the first 2 hrs, more than 60% of the drug contained in the sheets was released into the medium. Therefore, the rate-limiting step in delivery of the drug from the implant will not be determined by the polymeric composition, but rather by the solubility of the drug in the ocular membrane to which the implant will be affixed during therapy.

Pars Plana Drug Delivery Employing a Non-Biodegradable Implant

Gancyclovir was free-based from sterile gancyclovir sodium powder (Cryovene ™, Syntex) and incorporated into a polyurethane film as described above. the final loading value of the drug was 50%. A 3 mg piece of the gancyclovir/polyurethane implant was introduced into the pars plana of a rabbit eye. Drug release was monitored at defined time points by examining 50 μl samples taken from the vitreous. The drug content of the samples was determined by HPLC and the concentration of the drug in the vitreous calculated. The results are presented in Table 3.

TABLE 3

| Time Post-Implantation | Gancyclovir Concentration in Vitreous Segment (μg/ml) |
|---|---|
| 3 hrs | 0.34 |
| 24 hrs | 0.25 |
| 36 hrs | 0.18 |
| 96 hrs | 0.18 |

It is evident from the above results that biocompatible implants find effective use for treatment of a wide variety of ocular conditions. The implants provide for continuous administration of a drug over long periods of time, avoiding the need of a patient to administer drugs in much less effective ways, such as topically. In addition, treatments can be achieved by maintaining appropriately therapeutic levels of drugs in the eye, retaining the drug in the appropriate site and minimizing high concentrations throughout the host system which may have deleterious effects. Equilibration levels are rapidly achieved and maintained for long periods of time. Furthermore, one or only a few drug administrations may be required for treatments over extended periods of time, reducing the burden on the patient for self-administration, ensuring continued controlled medication, and minimizing the interference with the activities of the patient.

Polymeric encapsulation and/or incorporation of drags to produce implants protects doses of pharmacological agents from being diluted or degraded in the general circulation. The agents can be entrapped in various concentrations without any modifications. Encapsulation provides concentrated doses of medication which are more effective and less toxic than free drugs, while at the same time protecting the drugs from enzymatic attack or immune recognition. Placement of the implants over or within an avascular region of the eye avoids diffusion of the drug into the bloodstream and provides more direct, localized administration of drug to a site of interest, in this case a site within the posterior chamber. Direct administration to the posterior segment thus avoids the high concentrations of drug necessitated by systemic administration and the side affects which may be associated with such systemic administration.

The instant method provides an effective treatment for ocular diseases. The method is noninvasive in that it avoids injections into the interior of the eye, yet is able to provide a therapeutically effective amount of agent to a diseased site.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for treating an eye condition which comprises:
   preparing an implant by combining a physiologically active therapeutic agent and a permeability enhancing agent encapsulated in a pharmacologically acceptable biocompatible polymer; and
   introducing said implant extrinsic to the vitreous and incapable of migration from an implantation site, wherein said site is characterized by being avascular, permitting diffusion of a physiologically active agent from said implant into the vitreous, and in proximity to said eye condition,
   wherein said therapeutic agent is maintained at an effective dosage for said eye condition at the site of said eye condition for an extended period of time.

2. A method according to claim 1, wherein said biocompatible polymer is non-biodegradable.

3. A method according to claim 2, wherein said polymer is a polyurethane.

4. A method according to claim 2, wherein said polymer is an ethylene vinyl ester copolymer.

5. A method according to claim 4, wherein said ethylene vinyl ester copolymer is ethylene vinyl acetate.

6. A method according to claim 1, wherein said introducing step comprises introducing said implant into a suprachoroidal space, where the sclera is cut to expose the suprachoroid.

7. A method according to claim 6, wherein said suprachoroidal space is a surgically induced avascular region.

8. A method according to claim 1, where said introducing step comprises introducing said implant into the avascular pars plana.

9. A method according to claim 1, wherein said agent is an antitumor agent.

10. A method according to claim 1, wherein said agent is a bacterial agent.

11. A method according to claim 1, wherein said agent is a drug.

12. A method for treating an eye condition which comprises:
   preparing an implant by combining a physiologically active therapeutic agent and a permeability enhancing agent encapsulated in a pharmacologically acceptable biocompatible polymer; and introducing into the avascular pars plana of an eye said implant incapable of migration from said pars plana, wherein one implantation site is characterized by permitting diffusion of a physiologically active agent from said implant into the vitreous, and in proximity to said eye condition, wherein said agent is maintained at an effective dosage for said eye condition at the site of said eye condition for an extended period of time.

13. A method according to claim 9, wherein said implant is a plaque or particles.

14. A method according to claim 13, wherein said permeability enhancing agent is selected from the group consisting of at least one of isopropyl myristate, ethanol or oleic acid.

15. A method for treating choroidal tumors of an eye which comprises:

preparing an implant by combining an antitumor agent and a permeability enhancing agent encapsulated in a pharmacologically acceptable biocompatible polymer; and introducing into an avascular region of a suprachoroidal space of said eye said implant incapable of migration from said space, wherein said implant provides an effective dosage of said antitumor agent over an extended period of time.

16. A method according to claim 15, wherein said implant is a plaque having length and width dimensions of about 0.5 to 10 mm × 0.5 to 10 mm with a thickness of about 0.25 to 10 mm.

17. A method according to claim 16, wherein said antitumor agent is a member of the group consisting of methotrexate, vincristine, or a bacterial agent.

18. A method according to claim 17, wherein said antitumor agent is a bacterial agent, which is acid-fast bacilli.

19. A method according to claim 17, wherein said antitumor agent is *C. parvum*.

* * * * *